United States Patent
Ueno et al.

(10) Patent No.: US 6,475,803 B1
(45) Date of Patent: Nov. 5, 2002

(54) CYCLODEXTRIN DERIVATIVES AND MEASUREMENT OF WATER CONTAMINATION DEGREE USING THE SAME

(75) Inventors: Akihiko Ueno, Yokohama (JP); Juan Wang, Tokyo (JP)

(73) Assignees: Akihiko Ueno Japan (JP); Nihon Hels Industry Corporation (JP)

( * ) Notice: Subject to any disclaimer, the term of this patent is extended or adjusted under 35 U.S.C. 154(b) by 0 days.

(21) Appl. No.: 09/574,488

(22) Filed: May 19, 2000

(30) Foreign Application Priority Data

Aug. 23, 1999 (JP) .......................................... 11-234988
Sep. 10, 1999 (JP) .......................................... 11-295711

(51) Int. Cl.[7] .......................... G01N 21/64; C08B 37/16
(52) U.S. Cl. ...................... 436/166; 436/164; 436/172; 536/46; 536/103; 210/748
(58) Field of Search ................... 536/46, 103; 436/164, 436/172, 166; 210/748

(56) References Cited

U.S. PATENT DOCUMENTS

| | | | | |
|---|---|---|---|---|
| 4,726,905 A | * | 2/1988 | Friedman et al. ........... 210/692 |
| 4,939,388 A | * | 7/1990 | Eaton et al. ................. 307/427 |
| 5,190,663 A | * | 3/1993 | Fetzer ......................... 210/674 |
| 6,024,879 A | * | 2/2000 | Perly et al. ................. 210/635 |
| 6,063,287 A | * | 5/2000 | Smith et al. ................ 210/691 |
| 6,235,505 B1 | * | 5/2001 | Grull et al. .................... 435/98 |
| 6,271,039 B1 | * | 8/2001 | Palmer et al. .............. 436/166 |
| 6,391,946 B2 | * | 5/2002 | Wood et al. ............. 206/524.3 |

OTHER PUBLICATIONS

"Signal transduction in chemosensors of modified cyclodextrins" by Ueno et al. pp. 105–119.

"Review: fluorescent cyclodextrins for molecule sensing" by A. Ueno; Supramolecular Science, vol. 3, Nos. 1–3 1996; pp. 31–36.

Protein Nucleic Acid, Enzyme, vol. 41, No. 9, 1996, pp. 1407–1414.

* cited by examiner

Primary Examiner—Jill Warden
Assistant Examiner—Monique T. Cole
(74) Attorney, Agent, or Firm—Baker Botts LLP

(57) ABSTRACT

A cyclodextrin derivative is an X-hydroxynaphthalene-Y-amidated cyclodextrin formed by subjecting a starting cyclodextrin to an addition reaction with A-hydroxyl-B-carboxyl naphthalane and used for measuring the contamination degree of water.

2 Claims, 6 Drawing Sheets

Change of fluorescence intensity of cyclodextrin derivative 1 (■, ◆, ▼, ⊛) or 2 (□, ◇, ▽, *) in a buffer solution added with a halide ;
[ 1 ] = [ 2 ] = $1.0 \times 10^{-4}$ M ■, □ :dichloromethane ; ◆, ◇ :chloroform
▼, ▽ :dichloroethane ; ⊛, * :carbon tetrachloride Change of fluorescence intensity of cyclodextrin derivative 1 (■, ◆, ▼, ⊗) or 2 (□, ◇, ▽, ∗) in a buffer solution added with a halide ; [1] = [2] = $1.0 \times 10^{-4}$ M ■ 、□ : dichloromethane ; ◆ 、◇ : chloroform ▼ 、▽ : dichloroethane ; ⊗ 、∗ : carbon tetrachloride Change of fluorescence intensity of cyclodextrin derivative 1( ♠ ) or 2 ( ♤ )
in a buffer solution added with benzene ;
[ 1 ] = [ 2 ] = $1.0 \times 10^{-4}$ M Change of fluorescence intensity of cyclodextrin
derivative 1 (▲, ●) or 2 (△, ○)
in a buffer solution added with musty compound (or ordorants);
[1] = [2] = $1.0 \times 10^{-4}$ M ▲, △: dimethylisoborneol ; ●, ○: geosmin Change of fluorescence spectrum of a cyclodextrin derivative 1 in a buffer solution added with chloroform ; $\lambda ex=337nm$, [ 1 ]=$1.0 \times 10$ $M^{-4}$ Change of fluorescence spectrum of a cyclodextrin derivative 2 in a buffer solution added with chloroform ; $\lambda_{ex}=334$ nm, [2]$=1.0\times10^{-4}$ M Change of fluorescence spectrum of a cyclodextrin derivative 3 in a buffer solution added with chloroform ; $\lambda ex=295nm$, [ 3 ]=$5.0\times10^{-5}M$

CYCLODEXTRIN DERIVATIVES AND MEASUREMENT OF WATER CONTAMINATION DEGREE USING THE SAME

BACKGROUND OF THE INVENTION

1. Field of the Invention

This invention relates to cyclodextrin derivatives and a process for measuring a contamination degree of water by using the same, and more particularly to a process for measuring a contamination degree of water by using the cyclodextrin derivatives according to the invention to measure a contamination degree in a purifying cartridge used in a water purifier thereby to detect an exchanging time of the purifying cartridge.

2. Description of Related Art

As a method of purifying drinking water, there have been used various water purifiers. However, it is difficult to detect an exchanging time of a purifying cartridge used in such a purifier, so that it is the present condition that the lapse of constant time is the exchanging time instead of measuring the contamination degree of the purifying cartridge.

The inventors have made various studies with respect to the use of the fluorescent cyclodextrin derivative as a detecting substance (sensor) for measuring a contamination degree of water existing in our immediate surroundings from the old time, but satisfactory compounds could not be obtained.

A certain cyclodextrin derivative is selected from the cyclodextrin derivatives as examined above and dissolved in water and added with a given organic compound, which is exposed to a ultraviolet ray to measure a fluorescent intensity developed. As a result, it has been confirmed that naphthol-modified cyclodextrin tends to indicate a remarkable change in the fluorescence intensity as shown by graph showing a relation between an amount of the organic compound added and the fluorescence intensity. Now, the inventors have synthesized various cyclodextrin derivatives by changing a position of hydroxy group on a naphthol ring and made further studies in order to satisfy the above demand.

SUMMARY OF THE INVENTION

Under the above circumstance, the inventors have examined various cyclodextrin derivatives having naphthol ring and found out that novel cyclodextrin derivatives as mentioned later are excellent as a fluorescent substance.

According to a first aspect of the invention, there is the provision of a cyclodextrin derivative being an X-hydroxynaphthalene-Y-amidated cyclodextrin formed by subjecting a starting cyclodextrin to an addition reaction with A-hydroxyl-B-carboxyl naphthalane.

According to a second aspect of the invention, there is the provision of a process for measuring a contamination degree of water which comprises adding the cyclodextrin derivative defined in the first aspect of the invention as a host compound to water dissolving a slight amount of a contaminant therein and then irradiating a ultraviolet ray thereto to develop fluorescence at a given wavelength.

BRIEF DESCRIPTION OF THE DRAWINGS

The invention will be described with reference to the accompanying drawings, wherein.

DESCRIPTION OF PREFERRED EMBODIMENTS

Prior to the synthesis of the cyclodextrin derivative according to the invention, the studies leading to the success of the invention will be described below.

The following seven organic compounds (1)–(7) are selected as a target to be detected through fluorescence.

Dichloromethane (1)

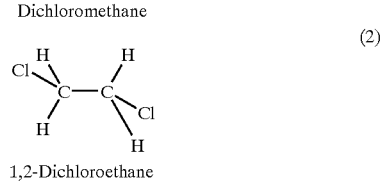
1,2-Dichloroethane (2)

Chloroform (3)

Carbon Tetrachloride (4)

-continued

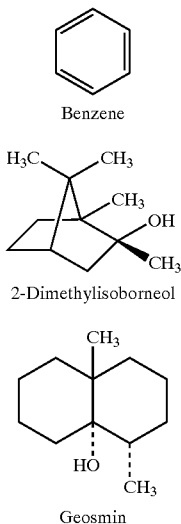

(5) Benzene (6) 2-Dimethylisoborneol (7) Geosmin

They are guest compounds included in the cavity of cyclodextrin and form a host-guest complex when the cyclodextrin derivative is a host molecule.

Each of the compounds (1)–(7) is added as a guest to an aqueous buffer solution of each of the following cyclodextrin derivatives 1 and 2 as a host, to which is irradiated a ultraviolet ray according to usual manner to measure a fluorescence intensity developed. The measured results are shown in FIGS. 1–3 while increasing an amount of each guest added.

In these figures, $\Delta I$ is a value of $I-I_0$, wherein $I_0$ indicates a fluorescence intensity at a constant wavelength ($\lambda$em) in case of adding no guest and I indicates a fluorescence intensity at a constant wavelength ($\lambda$em) in case of adding the guest. Moreover, $\lambda$em is 500 nm in case of the derivative 1 and 490 nm in case of the derivative 2.

Figure 1:
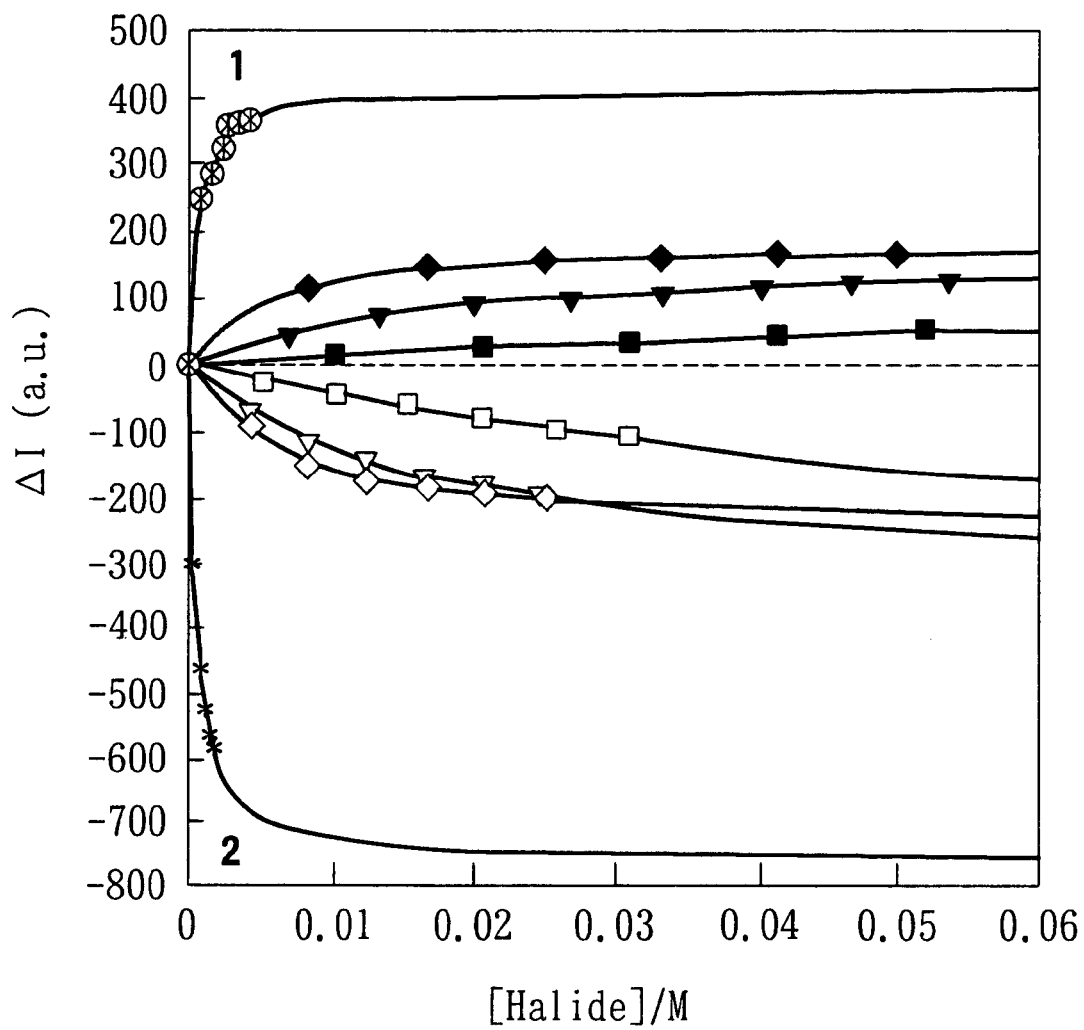
FIG. 1 is a graph showing a change of fluorescence intensity of a cyclodextrin derivative 1 or 2 according to the invention developed when a halide is added to an aqueous buffer solution of the derivative 1 or 2 and a ultraviolet ray is irradiated thereto according to usual manner in accordance with the increase of an amount of the halide added.
Figure 2:
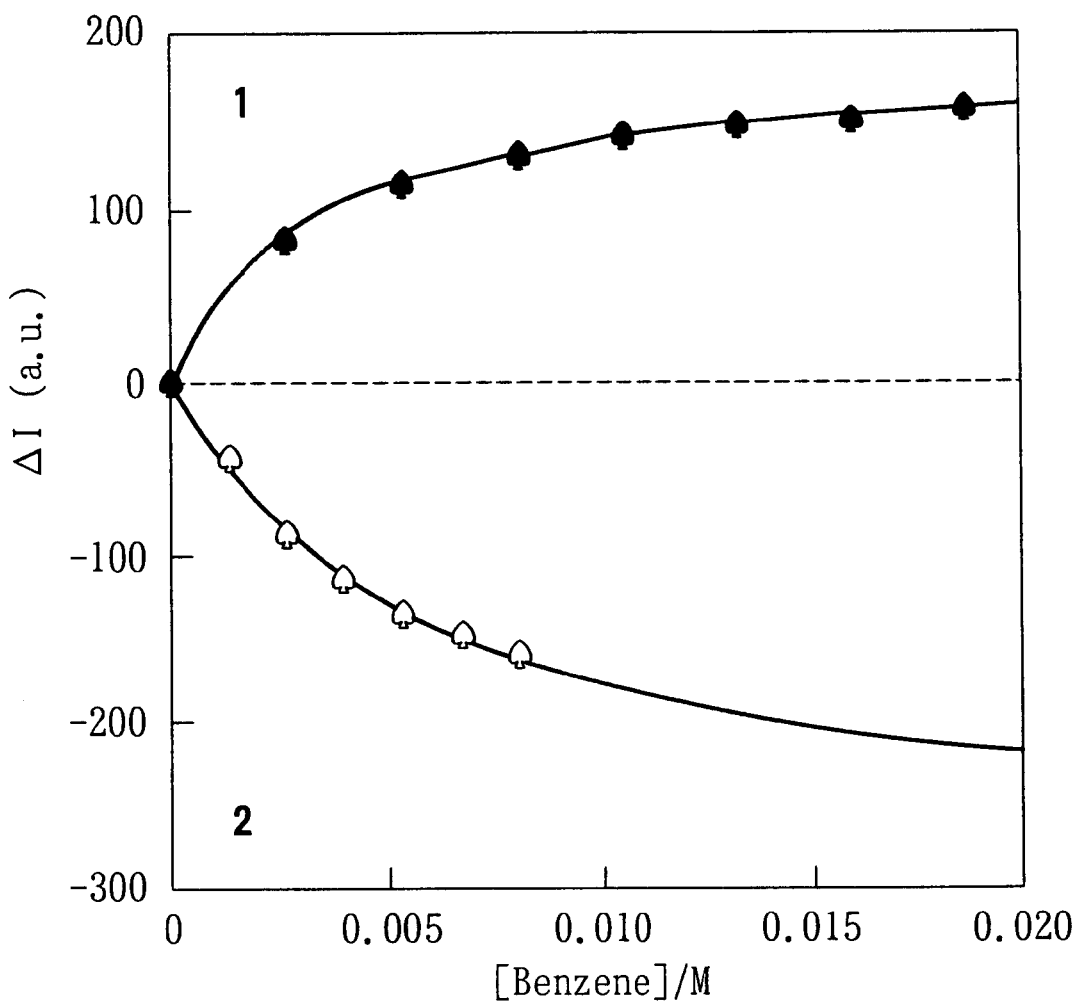
FIG. 2 is a graph showing a change of fluorescence intensity of a cyclodextrin derivative 1 or 2 according to the invention developed when benzene is added to an aqueous buffer solution of the derivative 1 or 2 and a ultraviolet ray is irradiated thereto according to usual manner in accordance with the increase of an amount of benzene added.
Figure 3:
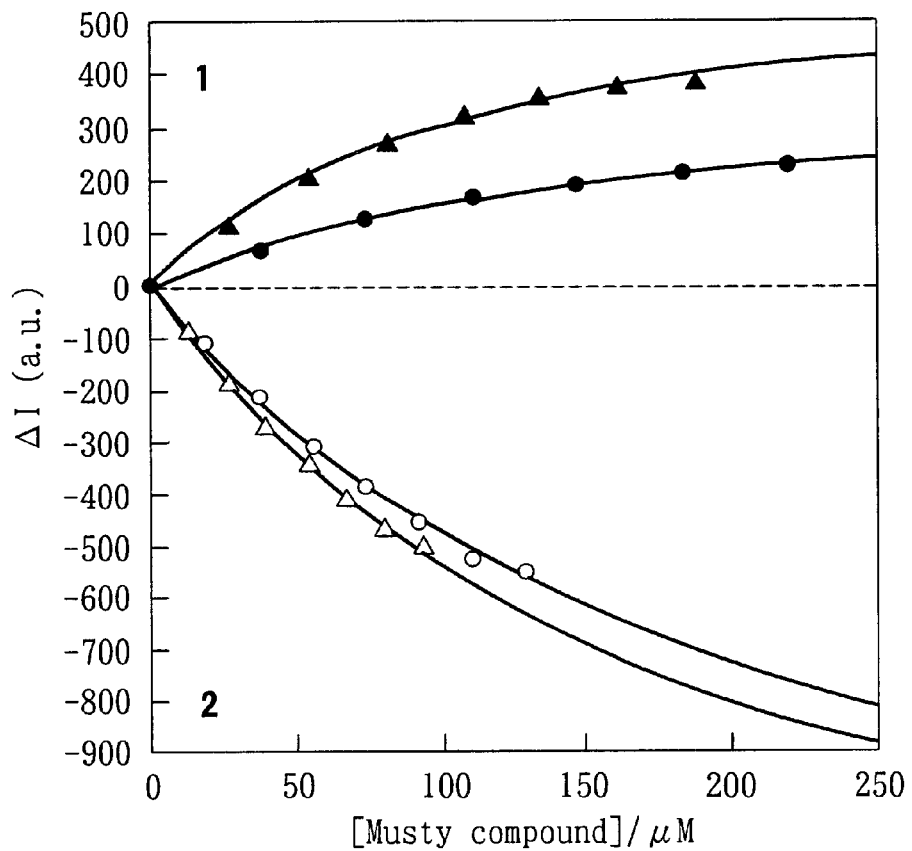
FIG. 3 is a graph showing a change of fluorescence intensity of a cyclodextrin derivative 1 or 2 according to the invention developed when a musty substance is added to an aqueous buffer solution of the derivative 1 or 2 and a ultraviolet ray is irradiated thereto according to usual manner in accordance with the increase of an amount of the musty substance added.

FIG. 1 is a $\Delta I$ curve in case of adding a halide such as dichloromethane, 1,2-dichloroethane, chloroform and carbon tetrachloride, and FIG. 2 is a $\Delta I$ curve in case of adding benzene, and FIG. 3 is a $\Delta I$ curve in case of adding 2-dimethylisobroneol and geosmin.

seen from the graphs of FIGS. 1–3, $\Delta I$ curve tends to increase in accordance with the increase of the addition amount of each guest in case of the derivative 1, while $\Delta I$ curve tends to decrease in accordance with the increase of the addition amount of each guest in case of the derivative 2. These results mean that the fluorescence intensity increases owing to the presence of the guest in case of the derivative 1, while the fluorescence intensity decreases due to the presence of the guest in case of the derivative 2.

Moreover, the change of fluorescence intensity is largest in 2-dimethylisobroneol and geosmin of FIG. 3 among these graphs, and particularly the change of fluorescence intensity in 2-dimethylisobroneol is large.

The details of the synthesis of the cyclodextrin derivatives according to the invention will be described below.

The inventors have confirmed that the fluorescence intensity of the host changes through the irradiation of the ultraviolet ray when the above organic compounds exist as a guest. Furthermore, it has been confirmed from these curves of fluorescence intensity that the change of fluorescence intensity increases according as the main chain (main nucleus) of the organic compound as the guest changes from straight to ring.

Incidentally, the inventors have confirmed that the fluorescence intensity increases when organic contaminants are added to an aqueous solution of a relevant naphthol derivative.

From the above facts, the inventors have considered that a compound formed by bonding naphthol unit to cyclodextrin increases or decreases the fluorescence intensity through the addition of the guest compound and synthesized cyclodextrin derivatives as follows.

The cyclodextrin derivatives according to the invention are derivatives 1, 2 and 3 as mentioned later.

| Structure of derivative molecule | Designation of compound | Abbreviation |
|---|---|---|
| Derivative 1: 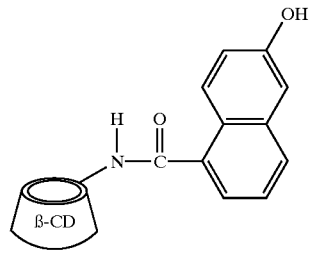 | 6-deoxy-6-(6-hydroxy-1-naphtho-amide)-β-cyclodextrin | 6,1-NAβCD |
| Derivative 2: 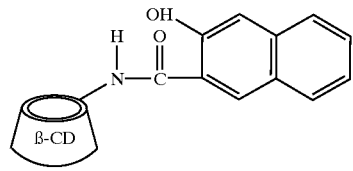 | 6-deoxy-6-(2-hydroxy-3-naphtho-amide)-β-cyclodextrin | 2,3-NAβCD |

| Derivative | Structure of derivative molecule | Designation of compound | Abbreviation |
|---|---|---|---|
| Derivative 3: | (β-CD)–HN–CH₂–CH₂–CH₂–CH₂–N(H)–C(O)–[naphthyl-OH] | 6-deoxy-6-[4-(6-hydroxy-1-naphtho-amide)butylamino]-β-cyclodextrin | 6,1-C₄-NAβCD |

Moreover, a hollow truncated cone used for the structure of the above cyclodextrin derivative schematically shows a steric structure of cyclodextrin and is frequently used by those skilled in the art (see *Protein, Nucleic Acid, Enzyme*, Vol. 41, No. 9, (1996) pp1407–1414). In the hollow truncated cone, an upper opening portion is a side of primary hydroxyl group and a lower opening portion is a side of secondary hydroxyl group.

In the above derivatives 1, 2 and 3, the position of OH may arbitrarily be changed on a naphthol ring of the cyclodextrin derivative. In the derivative 3, a compound having a carbon number of 1–10 may be used for bonding cyclodextrin to naphthol ring.

All of the derivatives 1–3 (1-NAβCD, 2,3-NAβCD and 6,1-C₄-NAβCD) are soluble in water. When a ultraviolet ray is irradiated to an aqueous solution of each of these derivatives, fluorescence is developed as previously mentioned. In this case, it has been confirmed that the fluorescence intensity curve shows a peak around 500 nm.

Each of these derivatives 1–3 is synthesized as follows:

filter. After the filtrate is left to stand over a night, it is filtered to obtain 10 g of a target white crystal. This compound is identified by TLC, mass spectrum and ¹H-NMR.

(b) Synthesis of 6-deoxy-6-amino-βCD(6-aminoβCD): 4.4 g of 6-O-Ts-βCD is dissolved in 50 ml of water and 2.5 g of NaN₃ is added to react at 80° C. for 4.5 hours as a suspension with stirring. When the reaction solution is transparent, the reaction is stopped once and concentrated and dried by means of a rotary evaporator to obtain a white solid. The white solid is dissolved in 50 ml of dimethyl formamide (DMF) and 2.5 g of triphenylphosphine is added to react at room temperature for 5 hours with stirring and then 8 ml of a concentrated ammonia solution is added to further react for 3 hours. After the completion of the reaction, the reaction product is reprecipitated with acetone and purified through a column chromatography using CM-Sephadex C25 as a column content to obtain 2.0 g of 6-amino-βCD. The compound is identified by TLC, mass spectrum and ¹H-NMR.

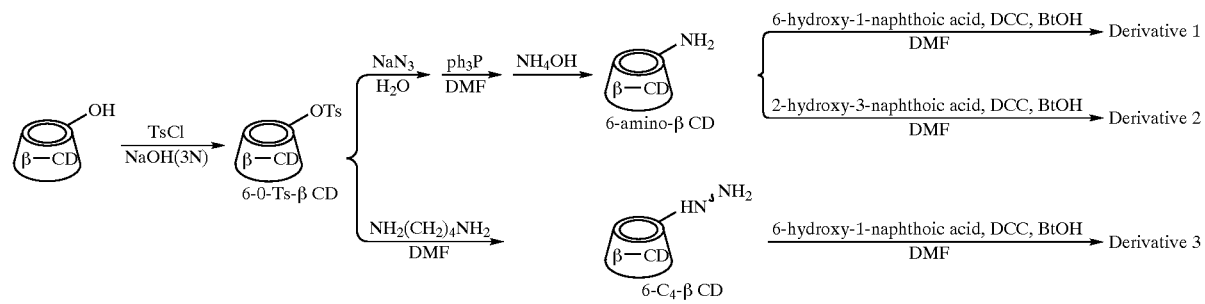

In the above synthesis of the derivatives 1–3, 6-O-Ts-βCD, 6-aminoβCD and 6-C4-βCD as an intermediate are synthesized as follows:

[Synthesis of each Intermediate]

(a) Synthesis of 6-O-tosyl-βCD(6-O-Ts-βCD): 44 g of β-CD is dissolved in 800 ml of an aqueous solution of 3N NaOH and 22 g of p-toluenesulfonyl chloride is added to react at 0–5° C. for 40 minutes with stirring. After the completion of the reaction, the reaction mixture is filtered through a glass filter and then the filtrate is neutralized with 3N HCl to precipitate a reaction product and thereafter the resulting precipitate is recovered and dried to obtain white powder. The white powder is dissolved in about 700 ml of water under heating and insoluble matter is removed through a glass (c) Synthesis of 6-C₄-βCD: 3.1 g of 6-O-Ts-βCD is added with 20.0 g of 1,4-diaminobutane and reacted at 70° C. for 18 hours with stirring. After the completion of the reaction, the reaction product is reprecipitated with acetone and purified through a column chromatography using CM-Sephadex C25 as a column content to obtain 2.0 g of 6-diaminobutane βCD (6-C₄-βCD). The compound is identified by TLC, mass spectrum and ¹H-NMR.

The synthesis process of each of the derivatives 1–3 using the above intermediates is as follows:

[Synthesis of Cyclodextrin Derivatives]

(a) Synthesis of derivative 1: 0.5 g of 6-amino-βCD is dissolved in 30 ml of DMF and 0.082 g of 6-hydroxy-1-naphthoic acid, 0.089 g of dicyclohexylcarbodiimide (DDC) and 0.058 g of hydroxybenzotriazole (HOBt) are added, which are stirred at 0° C. for 2 hours and reacted at room temperature for 70 hours. The reaction product is filtered and reprecipitated with acetone and further with chloroform to obtain 0.43 g of a crude product. Then, the crude product is purified through a column chromatography using Sephadex LH20 as a column content to obtain 0.30 g of light brown powder.

(b) Synthesis of derivative 2: The same procedure as in the derivative 1 is repeated except that 2-hydroxy-3-naphthoic acid is used instead of 6-hydroxy-1-naphthoic acid to obtain 0.14 g of a crude product. The crude product is purified to obtain 0.07 g of light beige powder.

(c) Synthesis of derivative 3: 0.5 g of 6-$C_4$-βCD is dissolved in 13 ml of DMF and 0.086 g of 6-hydroxy-1-naphthoic acid, 0.094 g of DDC and 0.062 g of HOBt are added, which are stirred at 0° C. for 2 hours and reacted at room temperature for 22 hours. The reaction product is filtered and reprecipitated with acetone and purified through a column chromatography using CM-Sephadex C25 as a column content to obtain 0.48 g of ivory powder.

Confirmatory analytical values of the derivatives 1–3 are shown in Table 1.

TABLE 1

| Derivative | $R_f$ | MS (m/z) | NMR (ppm) | Elementary analysis |
|---|---|---|---|---|
| 1 | 0.68 | calculated value: $[M + H]^+$ = 1305.8 | δ: 8.01(d, 1H; H-8'); 7.73(d, 1H; H-4'); 7.38(t, 1H; H-3'); 7.31(d, 1H; H-2'); 7.15(d, 1H; H-5'); 7.07(dd, 1H; H-7'); 5.95~4.75(m, 7H; H-1); | rational formula: $C_{53}H_{77}NO_{36}$·5.8$H_2O$·1.02DMF calculated value: |
| | | found value: $[M + H]^+$ = 1308.4 | 3.94~3.20(m, 42H; H-2~6)/($[D_6]$-DMSO). | C = 45.40%; H = 6.27%; N = 1.91%; C/N = 23.82 found value: |
| | | | | C = 45.40%; H = 6.51%; N = 1.91%; C/N = 23.80 |
| 2 | 0.68 | calculated value $[M + H]^+$ = 1305.8 | δ: 8.44(s, 1H; H-4'); 7.83(d, 1H; H-5'); 7.71(d, 1H; H-8'); 7.49(t, 1H; H-7'); 7.33(t, 1H; H-6'); 7.24(s, 1H; H-1'); 4.96~4.70(m, 7H; H-1); | rational formula: $C_{53}H_{77}NO_{36}$·8$H_2O$·0.94DMF calculated value: |
| | | found value: $[M + H]^+$ = 1307.3 | 3.98~3.20(m, 42H; H-2~H-6)/ ($[D_6]$-DMSO). | C = 44.12%; H = 6.26%; N = 1.79%; C/N = 24.66 found value: |
| | | | | C = 44.20%; H = 6.62%; N = 1.79%; C/N = 24.67 |
| 3 | 0.59 | calculated value: $[M + Na]^+$ = 1398.2 | δ: 8.11(d, 1H; H-8'); 7.77(t, 1H; H-4'); 7.48(t, 2H; H-2, 'H-3'); 7.25(dd, 1H; H-7'); 7.18(d, 1H; H-5'); 5.06~4.95(m, 7H; H-1); 3.96~3.35(m, 44H; H-2~5, H—$CH_2$N); | rational formula: $C_{57}H_{86}N_2O_{36}$·4$H_2O$ calculated value: |
| | | found value: $[M + Na]^+$ = 1398.5 | 3.12(d, H-1; H-6a/b); 2.87(dd; 1H; H-6b/a); 2.99(m, 2H; H—$NCH_2$); 1.8~1.6(m, 4H; H—$CH_2$)/($D_2O$). | C = 47.30%; H = 6.55%; N = 1.94%; C/N = 24.42 found value: |
| | | | | C = 47.13%; H = 6.83%; N = 1.93%; C/N = 24.44 |

[Properties of Derivatives]

The derivatives 1 and 3 are well soluble in water, while the derivative 2 is slightly difficult to be dissolved in water but is dissolved within a required concentration range in the detection. And also, these derivatives are easily dissolved by increasing pH of the aqueous solution.

In Table 1, TLC is carried out by using TLC plate (silica gel F254, layer thickness: 0.25 mm) made by Merck and a developing solvent comprising concentrated ammonia:ethyl acetate:2-propanol:water=1:3:5:4.

Naphthol unit as a light absorption unit is confirmed by irradiating a light of UV lamp to a developed plate to visually observe emission (fluorescence). Cyclodextrin portion is confirmed as a violet spot by spraying an Anis reagent (a 1:1 mixed solution of ethanol solution of 10% sulfuric acid and ethanol solution of anisaldehyde) onto the plate and heating by means of a heat gun.

$R_f$=(moving distance of derivative)/(developed distance of developing solvent)

The mass spectrum is measured by means of a mass spectrometer of MALDI III (TOF-MS) made by Shimadzu Seisakusho.

The measurement by $^1$H-NMR is carried out by using Varian VXR-500S FT-NMR spectrometer.

[Fluorescence Intensity of Each Derivative]

The fluorescence spectra are recorded on a Shimadzu RF-5300PC spectrofluorophotometer.

Moreover, the measuring conditions are as follows.

The derivative 1 is dissolved in the buffer solution of 0.005M $Na_2CO_3$—$NaHCO_3$ with pH at 9.28 so as to have a concentration of $1.0 \times 10^{-4}$M and an excitation wavelength ($\lambda$ex) at 25° C. is 337 nm.

The derivative 2 is dissolved in the buffer solution of 0.05M $KH_2PO_4$—NaOH with pH at 7.26 so as to have a concentration of $1.0 \times 10^{-4}$M and $\lambda$ex at 25° C. is 334 nm.

The derivative 3 is dissolved in a buffer solution of 0.005M $Na_2CO_3$—$NaHCO_3$ with pH at 9.28 so as to have a concentration of $5.0 \times 10^{-4}$M and $\lambda$ex at 25° C. is 295 nm.

As mentioned above, 6,1-NACD, 2,3-NAβCD and 6,1-C4-NAβCD according to the invention have hydrophilic nature and develop fluorescence when ultraviolet ray is irradiated to an aqueous solution of each of these derivatives. In this case, the fluorescence intensity curve indicates a peak around 500 nm.

Figure 4:
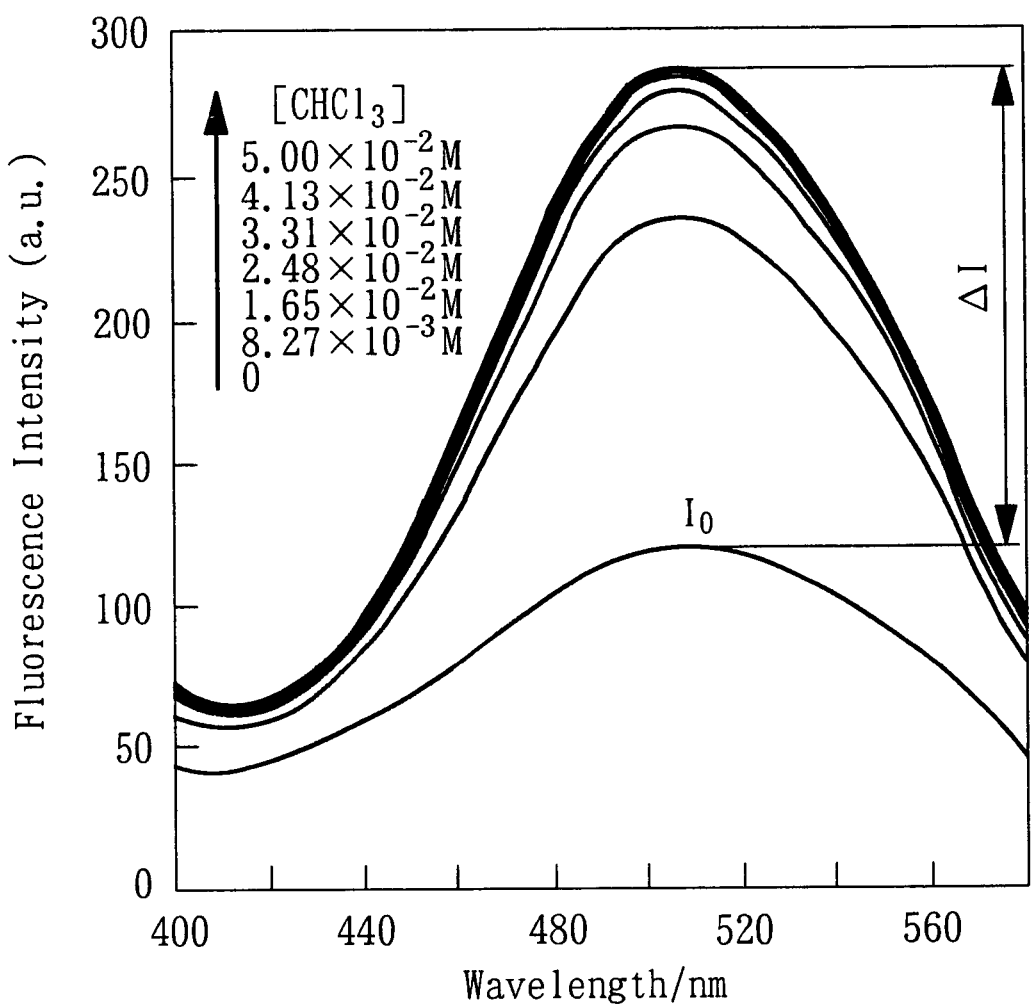
FIG. 4 is a graph showing a change of fluorescence spectrum of a cyclodextrin derivative 1 according to the invention in a buffer solution added with chloroform.
Figure 5:
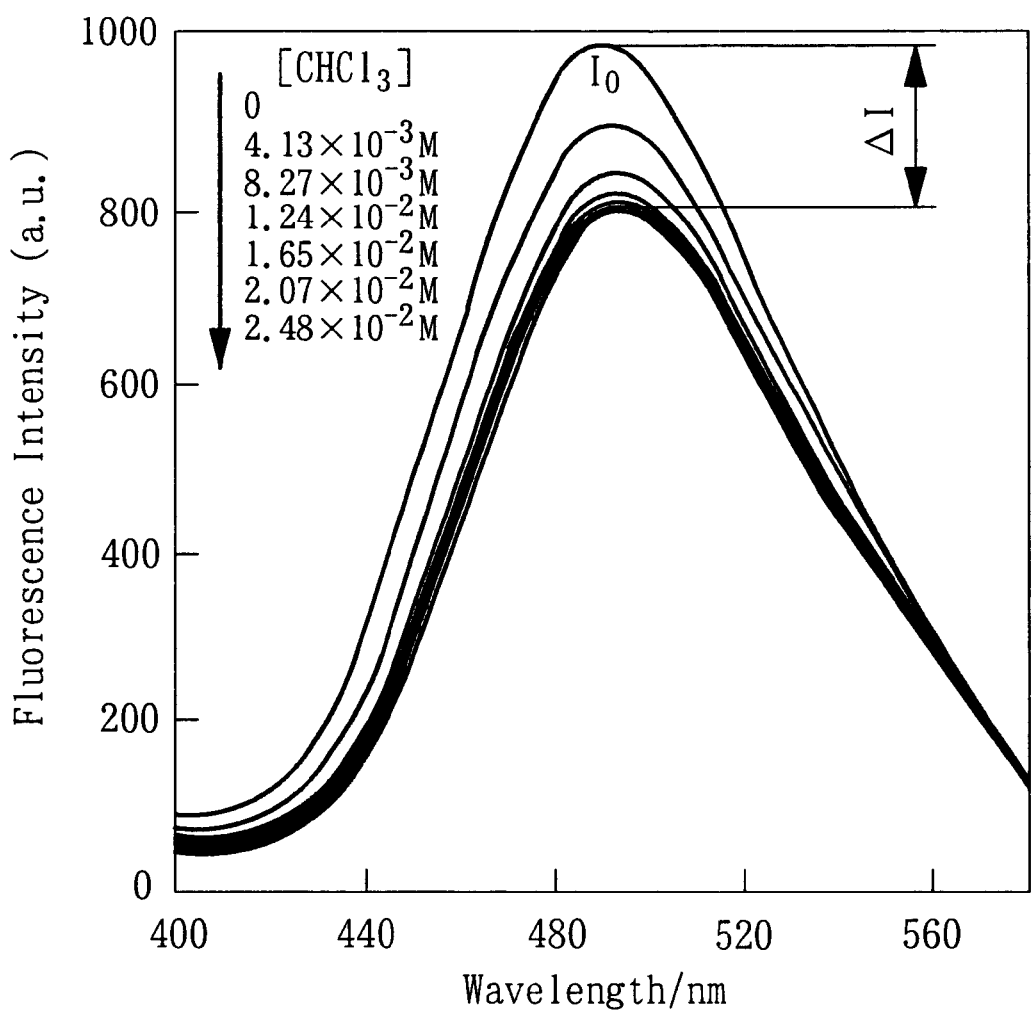
FIG. 5 is a graph showing a change of fluorescence spectrum of a cyclodextrin derivative 2 according to the invention in a buffer solution added with chloroform.
Figure 6:
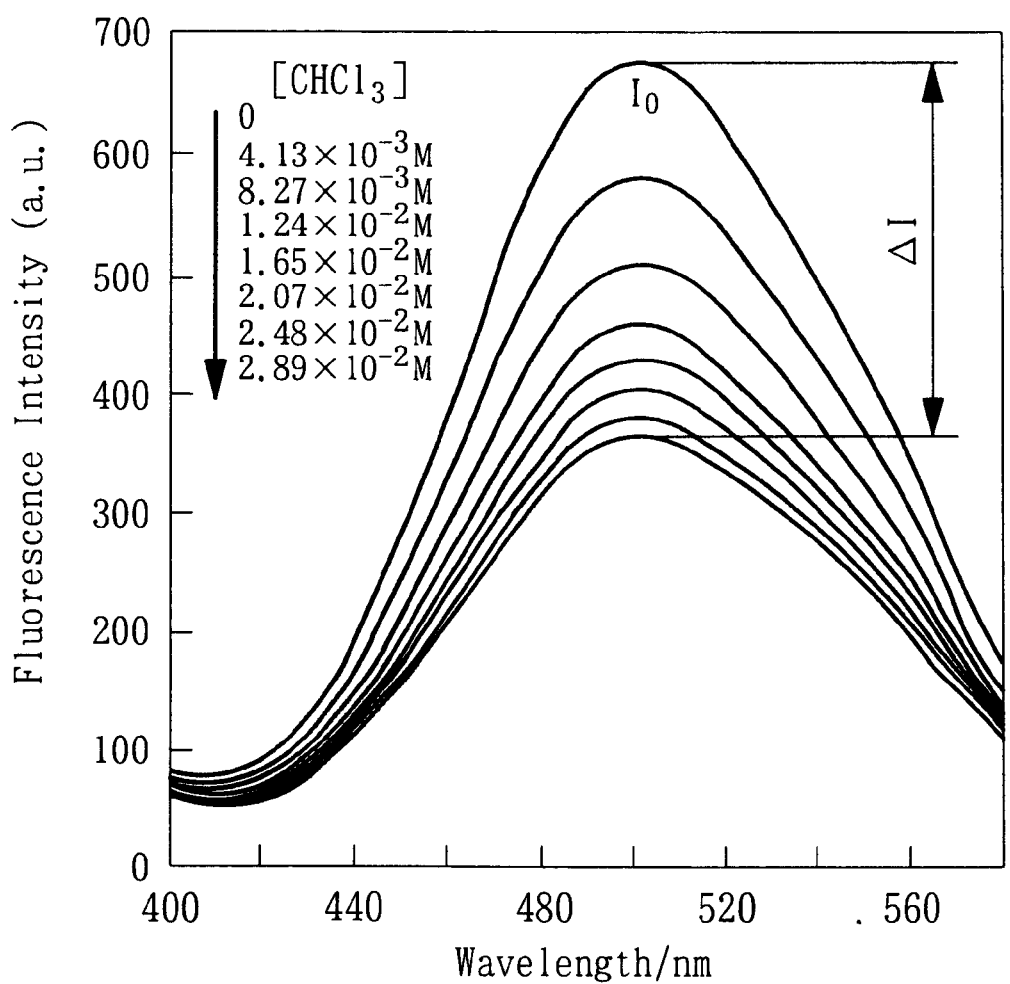
FIG. 6 is a graph showing a change of fluorescence spectrum of a cyclodextrin derivative 3 according to the invention in a buffer solution added with chloroform.

An artificial contamination experiment is carried out by adding chloroform to the buffer solution of each of the derivatives 1–3. The experimental results are shown in FIGS. 4–6, respectively.

As seen from the above experiments, the contamination degree of water can easily be known by measuring the fluorescence intensity of the cyclodextrin derivative according to the invention in the contamination of water.

Particularly, in the purification process of city water, it is possible to optically and rapidly measure the contamination degree without taking a long time or taking various operations as in the conventional technique, so that the invention is very effective to the control of water purification process and the like.

What is claimed is:

1. A cyclodextrin derivative being an X-hydroxynaphthalene-Y-amidated cyclodextrin formed by subjecting a starting cyclodextrin to an addition reaction with A-hydroxyl B-carboxyl naphthalene, wherein each of the variables X, Y, A, and B are absolute numbers corresponding to a position of a substituent.

2. A process for measuring a contamination degree of water comprising the steps of:

adding a predetermined amount of the cyclodextrin derivative of claim 1 as a host compound to a portion of the water containing a contaminant therein;

irradiating the portion of the water comprising the predetermined amount of the cyclodextrin derivative under an ultraviolet ray having a predetermined wavelength, wherein said predetermined wavelength varies depending on the cyclodextrin derivative added as the host compound;

measuring a first fluorescence intensity level developed from irradiating the portion of the water under the ultraviolet ray having the predetermined wavelength;

subsequently adding an equal predetermined amount of the cyclodextrin derivative to an equal portion of water containing no contaminant therein;

irradiating the no contaminant water comprising the predetermined amount of the cyclodextrin derivative under the ultraviolet ray having the predetermined wavelength;

measuring a second fluorescence intensity level developed from irradiating the no contaminant water under the ultraviolet ray having the predetermined wavelength; and determining a contamination level of the water by comparing the first fluorescence intensity level with the second fluorescence intensity level.

* * * * *